United States Patent
Dey et al.

(10) Patent No.: US 11,289,178 B2
(45) Date of Patent: *Mar. 29, 2022

(54) IDENTIFYING CHEMICAL SUBSTRUCTURES ASSOCIATED WITH ADVERSE DRUG REACTIONS

(71) Applicant: INTERNATIONAL BUSINESS MACHINES CORPORATION, Armonk, NY (US)

(72) Inventors: Sanjoy Dey, White Plains, NY (US); Achille Belly Fokoue-Nkoutche, White Plains, NY (US); Jianying Hu, Bronx, NY (US); Heng Luo, Ossining, NY (US); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 878 days.

This patent is subject to a terminal disclaimer.

(21) Appl. No.: 15/494,027

(22) Filed: Apr. 21, 2017

(65) Prior Publication Data

US 2018/0307804 A1    Oct. 25, 2018

(51) Int. Cl.
*G16C 20/70*   (2019.01)
*G16C 20/30*   (2019.01)
(Continued)

(52) U.S. Cl.
CPC .............. *G16C 20/70* (2019.02); *G16C 20/30* (2019.02); *G06N 3/04* (2013.01); *G06N 3/08* (2013.01)

(58) Field of Classification Search
CPC .......... G16C 20/70; G16C 20/30; G06N 3/04; G06N 3/08
See application file for complete search history.

(56) References Cited

U.S. PATENT DOCUMENTS

2002/0095261 A1   7/2002   Gut et al.
2009/0138204 A1   5/2009   Schwers et al.
(Continued)

FOREIGN PATENT DOCUMENTS

| | | |
|---|---|---|
| EP | 1211627 A1 | 5/2002 |
| WO | 2005047544 A1 | 5/2005 |
| WO | 2009108802 A2 | 3/2009 |

OTHER PUBLICATIONS

Mayr et al. ("DeepTox:Toxicity Prediction using Deep Learning", Frontiers in Environmental Science, Feb. 2, 2016, pp. 1-15) (Year: 2016).*

(Continued)

*Primary Examiner* — Miranda M Huang
*Assistant Examiner* — Robert Lewis Kulp
(74) *Attorney, Agent, or Firm* — Cantor Colburn LLP; Kristofer Haggerty (57) ABSTRACT

Embodiments of the present invention are directed to a computer-implemented method for generating a framework for analyzing adverse drug reactions. A non-limiting example of the computer-implemented method includes receiving to a processor, a plurality of drug chemical structures. The non-limiting example also includes receiving, to the processor, a plurality of known drug-adverse drug reaction associations. The non-limiting example also includes constructing, by the processor, a deep learning framework for each of a plurality of adverse drug reactions based at least in part upon the plurality of drug chemical structures and the plurality of known adverse-drug reaction associations.

8 Claims, 7 Drawing Sheets

(51) Int. Cl.
    *G06N 3/08*     (2006.01)
    *G06N 3/04*     (2006.01)

(56) References Cited

U.S. PATENT DOCUMENTS

2015/0134266 A1   5/2015   Cardozo et al.
2016/0140327 A1   5/2016   Hu et al.

OTHER PUBLICATIONS

Harpaz et al. ("Biclustering of Adverse Drug Events in FDA's Spontaneous Reporting System", Clin. Pharmocol Ter. Feb. 2011, 89(2):243-250) (Year: 2011).*

Kearnes et al. ("Molecular graph convolutions: moving beyond fingerprints", J. Computer Aided Mol. Des. (2016), vol. 30, pp. 595-608, Aug. 24, 2016) (Year: 2016).*

Xu et al. ("Deep Learning for Drug-Induced Liver Injury", J. Chem. Inf. Model, 2015, 55, 10, pp. 2085-2093) (Year: 2015).*

Louangrath et al. ("Correlation Coefficient According to Data Classification", SSRN Electronic Journal, 2014, pp. 1-28) (Year: 2014).*

Segler et al. ("Neural-Symbolic Machine Learning for Retrosynthesis and Reaction Prediction", ACS central science 2 (10), 2016, pp. 725-732) (Year: 2016).*

DuPrel et al. ("Choosing Statistical Tests", Deutsche Arzteblatt International, 107(19), 2010, pp. 343-348) (Year: 2010).*

Ivanov et al. ("In silico assessment of adverse drug reactions and associated mechanism", Drug Discovery Today, vol. 21, No. 1, Jan. 2016, pp. 58-71) (Year: 2016).*

Xu et al. ("Deep Learning Based Regression and Multi-class Models for Acute Oral Toxicity Prediction", https://arxiv.org/pdf/1704.04718v1.pdf, arXiv:1704.04718v1 [stat.ML] Apr. 16, 2017, pp. 1-36) (Year: 2017).*

Dougal Maclaurin ("Modeling, Inference and Optimization with Composable Differentiable Procedures", PhD Dissertation, Harvard University, Apr. 2016, pp. 1-135) (Year: 2016).*

Steven Michael Kearnes ("Fingind Needles in a Haystack: Molecular Similarity and Machine Learning for Drug Discovery Applications", PhD Dissertation, Stanford University, Jun. 2016, pp. 1-281) (Year: 2016).*

Mayr et al. (DeepTox: Toxicity Prediction using Deep Learning, Frontiers in Environmental Science, 3:80, Feb. 2, 2016, pp. 1-18) (Year: 2016).*

Bender A. et al., "Analysis of pharmacology data and the prediction of adverse drug reactions and off-target effects from chemical structure". ChemMedChem. 2007;2(6):861-73.

Cao DS, Xiao N, Li YJ, Zeng WB, Liang YZ, Lu AP, et al. "Integrating multiple evidence sources to predict adverse drug reactions based on a systems pharmacology model". CPT: pharmacometrics & systems pharmacology. 2015;4(9):498-506.

Cecile M. Krejsa et al, "Predicting ADME properties and side effects: The BioPrint approach", Article in Current opinion in drug discovery & development—Aug. 2003, pp. 1-12.

Duran-Frigola M. et al., "Analysis of chemical and biological features yields mechanistic insights into drug side effects". Chemistry & biology. 2013;20(4):594-603.

Izhar Wallach et al., "A Structure-Based Approach for Mapping Adverse Drug Reactions to the Perturbation of Underlying Biological Pathways", PLoS ONE, www.plosone.org., Aug. 2010, vol. 5, Issue 8, pp. 1-11.

Liu M. et al., "Determining molecular predictors of adverse drug reactions with causality analysis based on structure learning." Journal of the American Medical Informatics Association. 2014;21(2):245-51.

Pauwels E. et al., "Predicting drug side-effect profiles: a chemical fragment-based approach". BMC bioinformatics 2011;12(1):1.

Scheiber J. et al., "Mapping adverse drug reactions in chemical space". Journal of medicinal chemistry. 2009;52(9):3103-7.

Wang F. et al., "Exploring the associations between drug side-effects and therapeutic indications". Journal of biomedical informatics 2014;51:15-23.

Yamanishi Y. et al., "Drug side-effect prediction based on the integration of chemical and biological spaces". Journal of chemical information and modeling. 2012;52(12):3284-92.

Zhang W., et al., "Predicting drug side effects by multi-label learning and ensemble learning". BMC bioinformatics. 2015;16(1):1.

Sanjo Dey et al., "Identifying Chemical Substructures Associated With Adverse Drug Reactions", Related Application, U.S. Appl. No. 15/814,451, filed Nov. 16, 2017.

List of IBM Patents or Patent Applications Treated as Related; (Appendix P), Filed Nov. 27, 2017; pp. 1-2.

Duvenaud et al. ("Convolutional Networks on Graphs for Learning Molecular Fingerprints", Nov. 3, 2015, pp. 1-9) (Year: 2015).

* cited by examiner

IDENTIFYING CHEMICAL SUBSTRUCTURES ASSOCIATED WITH ADVERSE DRUG REACTIONS

BACKGROUND

The present invention generally relates to adverse drug reactions, and more specifically, to identifying chemical substructures associated with adverse drug reactions.

Adverse drug reactions (ADRs) are unintended and harmful reactions caused by normal uses of drugs. ADRs represent a significant public health problem all over the world. In the United States, it is estimated that over 2 million serious ADRs occur among hospitalized patients, resulting in over 100,000 deaths each year. Moreover, ADRs are a contributing factor to the high expenditure and low effectiveness of laboratory-based pharmaceutical drug development. Readily available information in the early stages of drug development can often be limited to the chemical structure of a drug candidate. However, predicting and preventing ADRs in the early stage of the drug development pipeline can help to enhance drug safety and reduce financial costs associated with drug discovery.

Finding novel associations between chemical substructures and ADRs could guide research efforts toward drug candidates that are more likely to lead to safe and efficacious drugs. For instance, if a chemical substructure is determined to be associated with ADRs, researchers could design drug candidates that do not incorporate such substructures. Elucidating such detailed relationships among chemical substructures and ADRs could infer new knowledge for domain experts, for instance, that could be utilized to redesign a drug under development and, thus, increase investigative efforts leading to viable candidates.

SUMMARY

Embodiments of the present invention are directed to a computer-implemented method for generating a framework for analyzing adverse drug reactions. A non-limiting example of the computer-implemented method includes receiving to a processor, a plurality of drug chemical structures. The non-limiting example also includes receiving, to the processor, a plurality of known drug-adverse drug reaction associations. The non-limiting example also includes constructing, by the processor, a deep learning framework for each of a plurality of adverse drug reactions based at least in part upon the plurality of drug chemical structures and the plurality of known adverse-drug reaction associations. Such computer-implemented methods can enable a-priori identification of chemical substructures likely to result in ADRs.

Embodiments of the invention are directed to a computer program product for analyzing adverse drug reactions. A non-limiting example of the computer program product includes a computer readable storage medium having program instructions embodied therewith. The program instructions are executable by a processor to cause the processor to perform a method. A non-limiting example of the method includes receiving a plurality of drug chemical structures. The non-limiting example also includes receiving a plurality of known drug-adverse drug reaction associations. The non-limiting example also includes constructing a deep learning framework for each of a plurality of adverse drug reactions based at least in part upon the plurality of drug chemical structures and the plurality of known adverse-drug reaction associations. Such computer program products can enable a-priori identification of chemical substructures likely to result in ADRs.

Embodiments of the invention are directed to a processing system for analyzing adverse drug reactions. A non-limiting example of the processing system includes a processor in communication with one or more types of memory. The processor can be configured to receive a plurality of drug chemical structures. The processor can also be configured to receive a plurality of known drug-adverse drug reaction associations. The processor can also be configured to construct a deep learning framework for each of a plurality of adverse drug reactions based at least in part upon the plurality of drug chemical structures and the plurality of known adverse-drug reaction associations. Such processing systems can enable a-priori identification of chemical substructures likely to result in ADRs.

Embodiments of the present invention are directed to a computer-implemented method for predicting chemical substructures associated with adverse drug reactions. A non-limiting example of the computer-implemented method includes generating a plurality of raw drug features. The non-limiting example also includes pooling the plurality of significant substructures into a plurality of fixed-sized vectors. The non-limiting example also includes generating a plurality of fixed-length fingerprint representations based at least in part up on the plurality of fixed-sized vectors. The non-limiting example also includes building a final predictive model based at least in part upon the fixed-length fingerprint representations. Such methods can generate accurate chemical fingerprints associated with known ADRs.

Embodiments of the present invention are directed to a system for predicting chemical substructures associated with adverse drug reactions. A non-limiting example of the system includes a drug-ADR association prediction module. A non-limiting example of the system also includes a significant association identification module. A non-limiting example of the system also includes a neighborhood substructure association module. A non-limiting example of the system also includes a grouping module. Such systems can generate accurate chemical fingerprints associated with known ADRs.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are intended to include any integer number greater than or equal to one, i.e. one, two, three, four, etc. The terms "a plurality" are intended to include any integer number greater than or equal to two, i.e. two, three, four, five, etc. The term "connection" is intended to include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Figure 1:
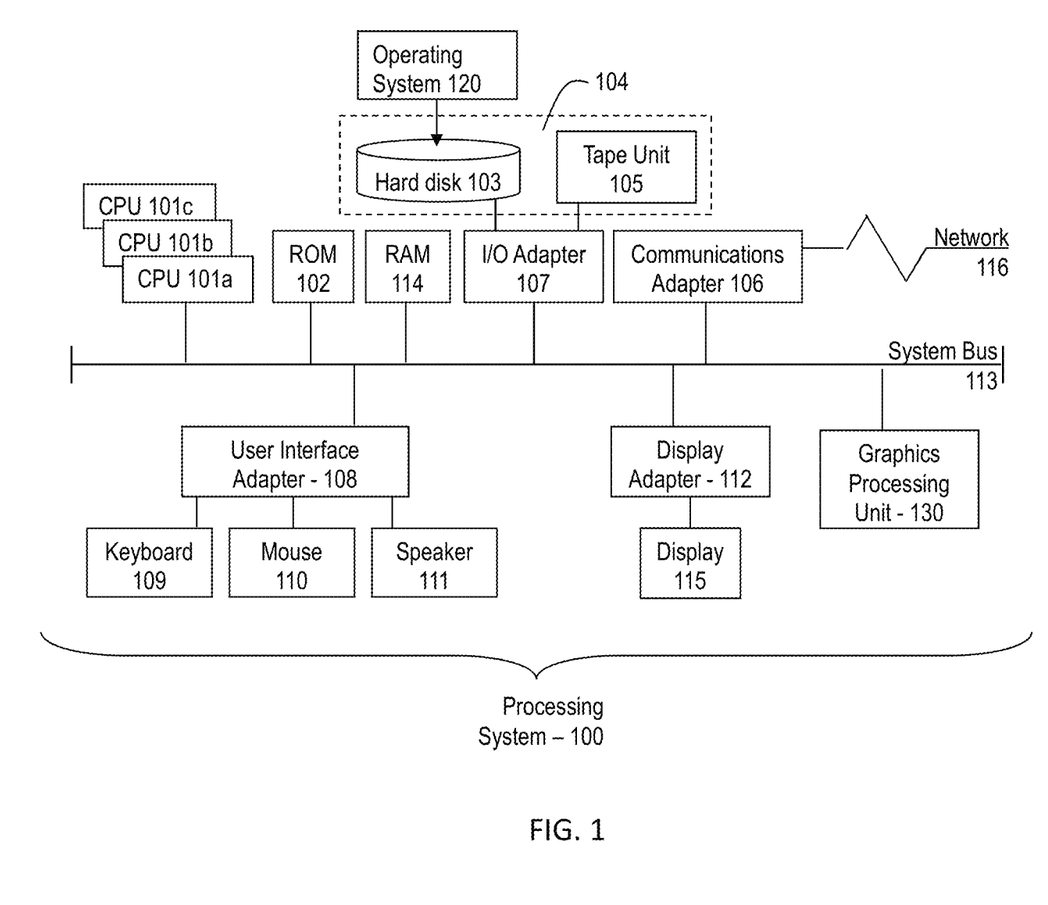
FIG. 1 depicts a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments of the invention, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Turning now to an overview of technologies that are more specifically relevant to aspects of the invention, according to the World Health Organization (WHO), an ADR is generally defined as an unintended and harmful reaction suspected to be caused by a drug taken under normal conditions. Identifying potential ADRs of drug candidates in the early stage of the drug development pipeline can improve drug safety, reduce risks for patients, and reduce monetary costs to pharmaceutical companies.

Information available in the early stages of drug development can be largely limited to the chemical structure of the drug candidate. The molecular structures of drugs can be leveraged in drug development where specific chemical substructures of drugs responsible for the ADRs can be identified. Thus, some existing studies on ADR prediction have focused on analyzing the chemical properties of drug molecules. Elucidating such detailed relationships between such chemical substructures and ADRs has potential to infer new knowledge for domain experts that can be used to redesign a drug under development and, thus, increase drug efficacy while minimizing the risk to patients and monetary expenditure associated with research and development. However mechanisms of ADRs can be complicated and not well understood presenting several challenges.

In some embodiments of the invention, each drug molecule can be represented in a suitable feature vector based upon its chemical structure and machine learning can be leveraged to predict ADRs a-priori. Some embodiments of the invention and have the capability of exploring all possible chemical substructures available in a set of drugs or drug candidates.

Embodiments of the invention advantageously provide a neural fingerprint method in a simultaneous deep learning framework for ADR prediction such that label information (including drug-ADR associations) can be used in the feature generation stage of a machine learning process. Some embodiments of the invention include interpretation and analysis of generated features to evaluate their associations for the prediction of ADRs in new drugs.

Turning now to an overview of the aspects of the invention, one or more embodiments of the invention address the above-described shortcomings of the prior art by providing a methodology and system for identifying substructures of chemical compounds that have significant associations with ADRs using a machine learning approach. Embodiments of the invention can systematically identify sub structures of chemical compounds that have significant association with ADRs, which can provide actionable insights for drug design. "Significant association" as used herein means an association that is statistically significant as determined by one or more statistical methods. Embodiments of the present invention can provide additional insights concerning the underlying reasons that certain substructures can induce ADRs in addition to predicting ADRs from drugs and drug candidates.

The above-described aspects of the invention address the shortcomings of the prior art by ranking substructure-ADR pairs obtains from generated models to systematically analyze the relationships among groups of chemical substructures within groups of related ADRs using bi-clustering based machine learning techniques. Through such techniques, drug discovery efforts can include the redesign of specific parts of identified substructures of a drug in response to and/or in connection with the relationship analysis.

Figure 2:
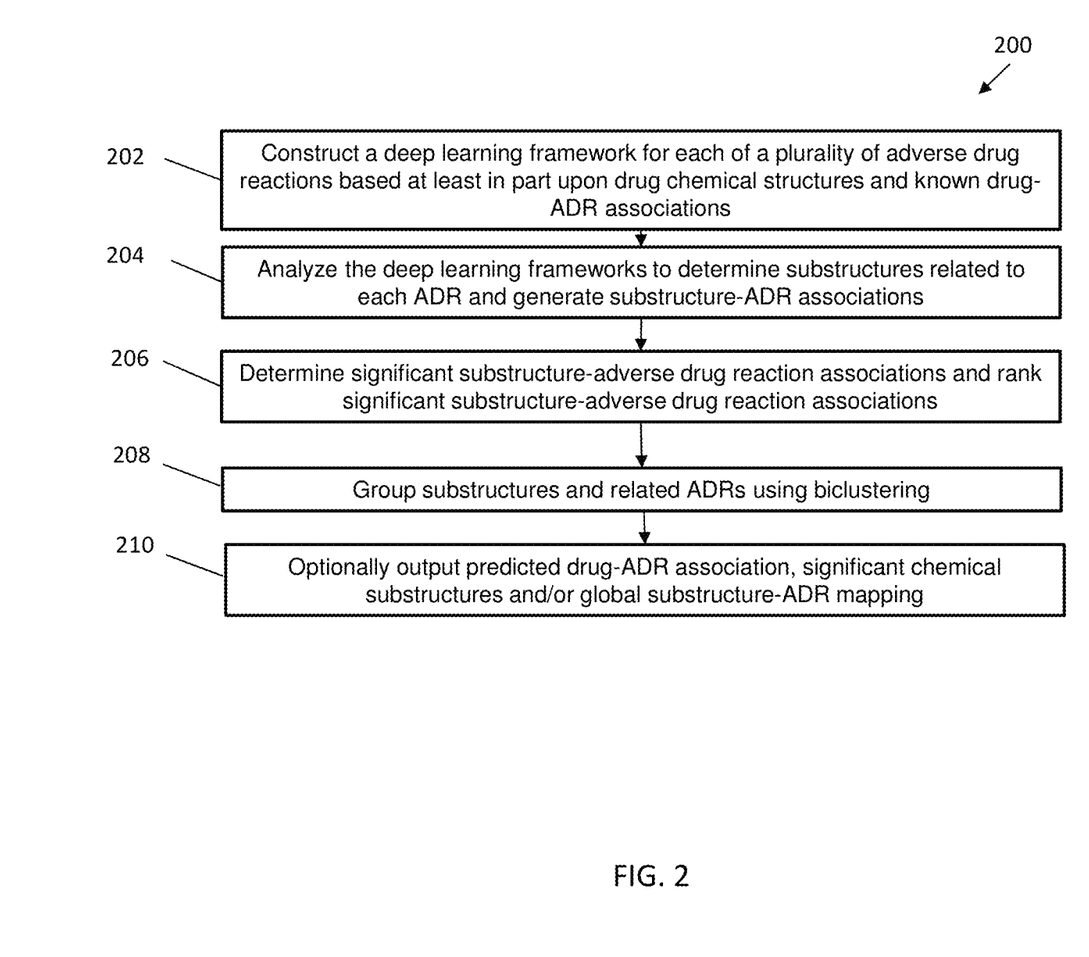
FIG. 2 depicts a flow diagram of a method according to one or more embodiments of the present invention.

Turning now to a more detailed description of aspects of the present invention, FIG. 2 depicts a method 200 of identifying chemical substructures associated with ADRs according to one or more embodiments of the present invention. As is shown, the method 200 includes constructing a deep learning framework for each of a plurality of ADRs based at least in part upon drug chemical structures and known drug-ADR associations as shown at block 202. As used herein, "drug chemical structure" is understood to mean the complete chemical structure of a pharmaceutical drug or candidate pharmaceutical drug. Known drug-ADR associations include ADRs known to be associated with a drug through clinical testing, therapeutic administration, and the like. The method 200 also includes, as shown at block 204, analyzing the deep learning framework to determine substructures related to each ADR and generate substructure-ADR associations. As used herein, "substructure" is intended to mean a portion of a chemical structure of a chemical compound. The method 200 also includes, as shown at block 206, determining significant substructure-ADR associations and ranking the significant substructure-ADR associations. The method 200 also includes, as shown at block 208, grouping substructures and related ADRs using biclustering. Optionally, the method 200 includes outputting predicted drug-ADR associations, significant chemical substructures, and/or global substructure-ADR mapping as shown at block 210.

The deep learning framework can include a neural fingerprint based predictive model. In some embodiments of the invention, a convolutional neural fingerprint framework is generated wherein the neighborhood of each atom is explored iteratively based upon hidden layers by representing a drug in either a 2D or a 3D graph. ADR prediction can be formulated as a binary prediction problem, wherein a predictive model is built for each ADR using chemical fingerprints as features.

In some embodiments of the invention, constructing a deep learning framework for each of a plurality of ADRs based at least in part upon drug chemical structures and known drug-ADR associations. Drug chemical structures and known drug-ADR associations can be obtained automatically or manually. Public databases contain a variety of information regarding known drugs and ADRs, including chemical structural data and chemical data. These information sources can contain structured or unstructured data. Drug chemical structures and known drug-ADR associations can include structured data, unstructured data, or both structured and unstructured data. As used herein, structured data includes data that is categorized or grouped in accordance with a system of defined rules. As used herein, unstructured data includes data that is not categorized or grouped in accordance with a system of defined rules. For example, unstructured data includes, but is not limited to, data published in journal articles in a narrative format. In exemplary embodiments, known drug data includes data from databases generally known to persons of ordinary skill in the art. For example, known drug data can include data from the DrugBank database, UniProt, Unified Medical Language System TM, PubMed, and/or various scientific journals, including, but not limited to, the Journal of Clinical Oncology, JAMA, BJC, and Clinical Infectious Diseases. Adverse drug event data includes information related to adverse events associated with a drug. Adverse drug event data can include, for example, the incidence, prevalence, or severity of events such as bleeding, paralysis, hyperkalemia.

Figure 3:
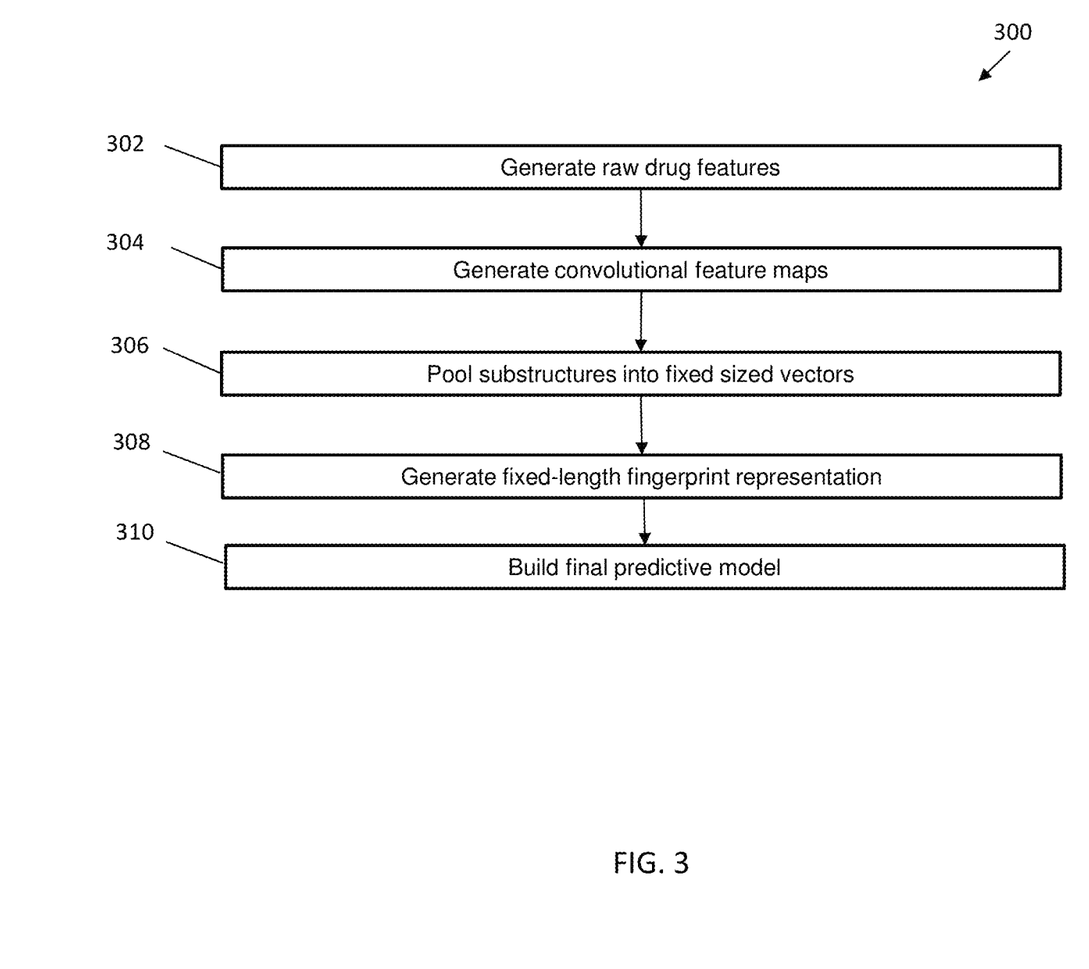
FIG. 3 depicts a flow diagram of a method according to one or more embodiments of the present invention.

FIG. 3 depicts an exemplary method 300 for constructing a deep learning framework for a plurality of adverse drug reactions according to one or more embodiments of the present invention. The method 300 includes, as shown at block 302, generating raw drug features. The method 300 also includes, as shown at block 304, generating convolutional feature maps. The method 300 also includes pooling substructures into fixed sized vectors, as shown at block 306. The method 300 also includes, as shown at block 308, generating fixed-length fingerprint representations. The method 300 also includes, as shown at block 310, building a final predictive model.

Embodiments of the invention including generating raw drug features can include, for instance, representing each drug into a 2D or 3D graphical structure. After generation of the graphical structure, in some embodiments of the invention, chemical features for each constituent atom in the drug can be extracted. For example, known fingerprint algorithms, such as ECFP, can be used to derive one or more features such as atomic element, degree, numbers of attached hydrogen atoms, implicit valence, aromaticity indicator, and/or bond type. Each drug can be represented by a matrix $X \in R^{n_x \times d}$, where $n_x$ represents the number of atoms in drug X and d is the total number of features for each atom. Let $x_i \in R^d$ represent the feature vector of each atom $i \in \{1, \ldots, n_x\}$.

Some embodiments of the invention include generating convolutional feature maps. A convolutional step can, for instance, represent a substructure in a particular layer into a condensed feature vector. In each interaction, or layer, of the algorithm, each substructure in current layer l (represented by each atom i referred as center and any neighbors explored in previous layers) can be expanded to include the immediate neighbors of each atom belonging to that substructure. Subsequently, all atomic features and bonding information of the atoms included within the substructure from previous layers can be concatenated into a large feature vector of size $d_{l-1}$ and redefined as new feature vector $x_i^{l-1} \in R^{d_{l-1}}$.

Each substructure can be obtained by starting the search from multiple atoms belonging to substructures and, thus, can be obtained from multiple centers. To remove resultant redundancies, each substructure $x_i^{l-1}$ can be mapped into lower dimensions using a single layer of neural network with $d_{l-1}$ input nodes and $d_l$ output nodes. A weight matrix of $H \in R^{d_l \times d_{l+1}}$ can be defined as follows: $x_i^l = f(x_i^{l-1} H + b)$ where $b \in R$. In this instance, f is a smoothing function to reduce susceptibility to minor variations in substructure.

Some embodiments of the invention include pooling multiple substructures into fixed sized vectors. For example, after generation of convolutional features maps in each level, similar substructures can be pooled into a fixed-sized feature vector of size K (hyper-parameter) using another level of neural network of weights F and a softmax, for instance, which has been shown to have a concise set of fingerprint representations for larger drug molecules. A simple addition function can be used to summarize the activation score of each atom that belongs to a given molecule in the pooling stage of the convolutional neural network.

In some embodiments of the invention, steps of generating convolutional feature maps and pooling multiples substructures into fixed-sized vectors are iterated for each radius of the molecule up to a maximum radius of the substructure L using a separate hidden layer to successively explore all possible substructures up to a maximum path length of 2L−1. Thereafter, in some embodiments of the invention, fingerprint vectors obtained from each layer are pooled (or summarized) into a final representation by summing them into a final fixed-length fingerprint representation.

Embodiments of the invention include building final predictive models. In some embodiments of the invention, upon generation of a final fingerprint representation for each drug, a fully connected neural network can be used to evaluate the ability to predict an ADR. For each ADR, for example, drugs associated with the ADR can be labeled as positives and the remaining drugs can be labeled as negatives. A predictive model can be built, for instance, using L2-norm regularized logistic regression separately for each ADR using final fingerprint representations as features. A loss function can be describe according to the following formula:

$$\mathcal{L}(Z, y, w) = \sum_i (y_i - f(z_i * w + b)) + \lambda \|w\|_2^2$$

wherein, Z is the matrix containing all fingerprints for each drug denoted as $z_i \in R^W$, is a maximum radius for substructures, K is the number of fingerprints with the best F-1 score, $\lambda$ is a regularization parameter, and f is a non-linear function (for example rectification with rectified linear unit (ReLU)). Batch normalization can be used to optimize each batch of size 100 using a known algorithm, such as ADAM. Hyper-parameters of the algorithms such as $\lambda$, R, K, can be selected during cross-validations. Further tuning of parameters can be performed for neural fingerprints based upon F1-scores, such as the numbers of neurons in the hidden layers and in the final layer.

Embodiments of the invention can include generating substructure-ADR associations. Extraction and interpretation of the important fingerprints of drugs can provide useful information concerning ADRs. For example, known ADRs can be analyzed with the deep learning framework to by determine substructures related to each ADR by identifying the top predictive fingerprints based upon learned weights from the final layer of the neural network. For each of the top predictive fingerprints, each layer can be investigated to identify atoms and associated drug molecules having the highest activation for the fingerprint during a first convolution step. Subsequently, substructures can be reconstructed by using the identified atom as center and expanding the neighborhood up to the associated layer.

Figure 4:
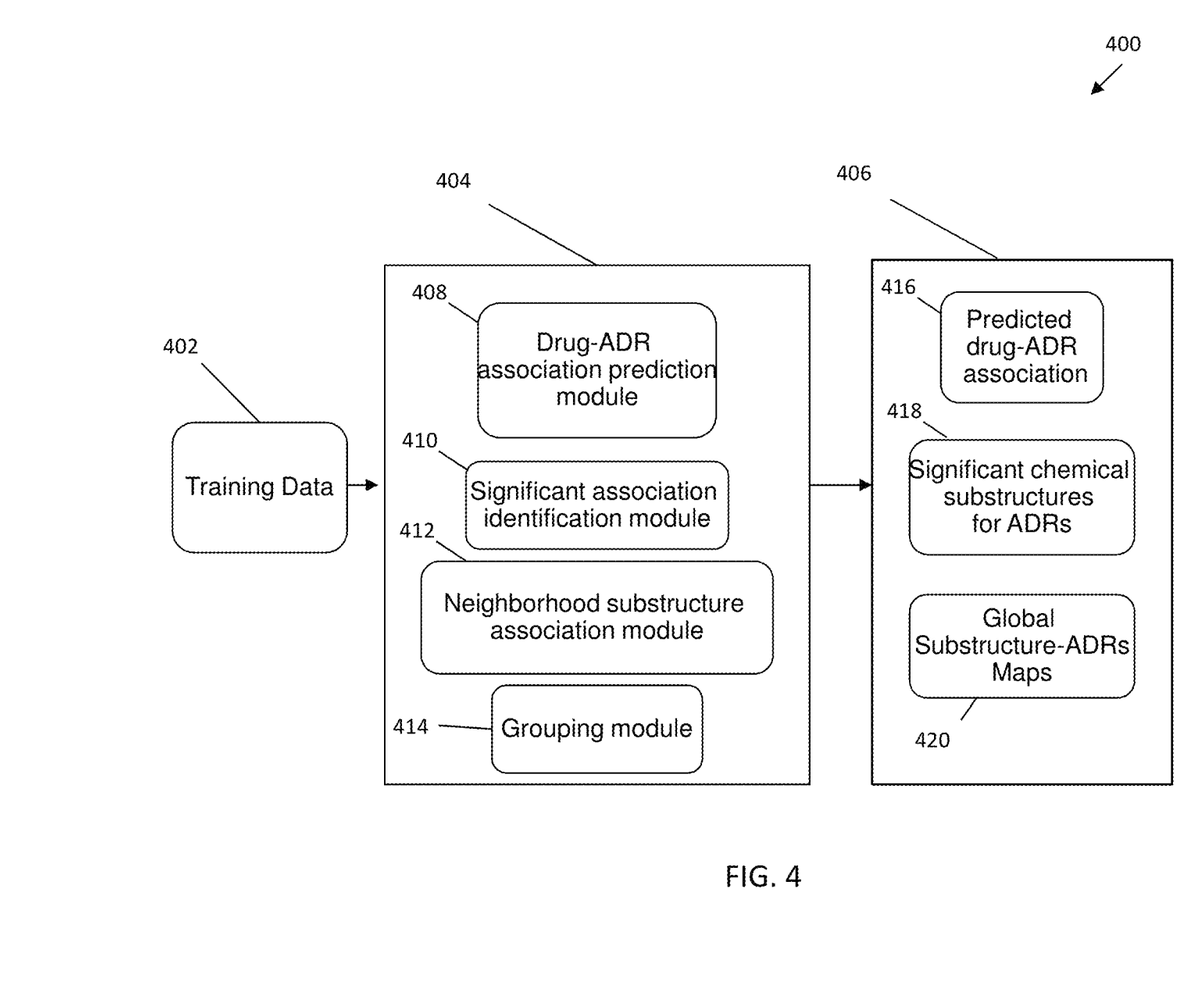
FIG. 4 depicts an exemplary system according to one or more embodiments of the present invention.

FIG. 4 depicts an exemplary system 400 for identifying chemical substructures associated with ADRs according to one or more embodiments of the present invention. The system 400 includes an input including training data 402, a deep learning ADR prediction hub 404, and an output 406. Training data can include, for instance, chemical structures of drugs as represented by neighborhood-based fingerprints and already known drug-ADR associations. In some embodiments, not illustrated in FIG. 4, the system can include optional input, such as domain knowledge about potential substructures of ADRs or existing relationships among substructures of drugs. The ADR prediction hub 404 can include a drug-ADR association prediction module 408, a significant association identification module 410, a neighborhood substructure association module 412, and/or a grouping module 414. The output 406 can include, for example, a predicted drug-ADR association 416. The output 406 can also include significant chemical substructures for ADRs 418. "Significant chemical substructures" as used herein means chemical substructures that have a statistically significant association with an ADR. The output 406 can also include global substructure-ADR maps 420.

In some embodiments of the invention, drug-ADR association prediction module 408 can construct a deep learning framework for each of a plurality of ADRs based at least in part upon drug chemical structures and known drug-ADR associations.

Significant association identification module 410 can analyze the deep learning frameworks to determine substructures related to each ADR and generate substructure-ADR associations.

Neighborhood substructure association module 412 can determine significant substructure-adverse drug reaction associations, for example with a chi-squared test, and rank significant substructure-adverse drug reaction associations, for example, according to statistical significance.

Grouping module 414 can group substructures and related ADRs using biclustering.

Figure 5:
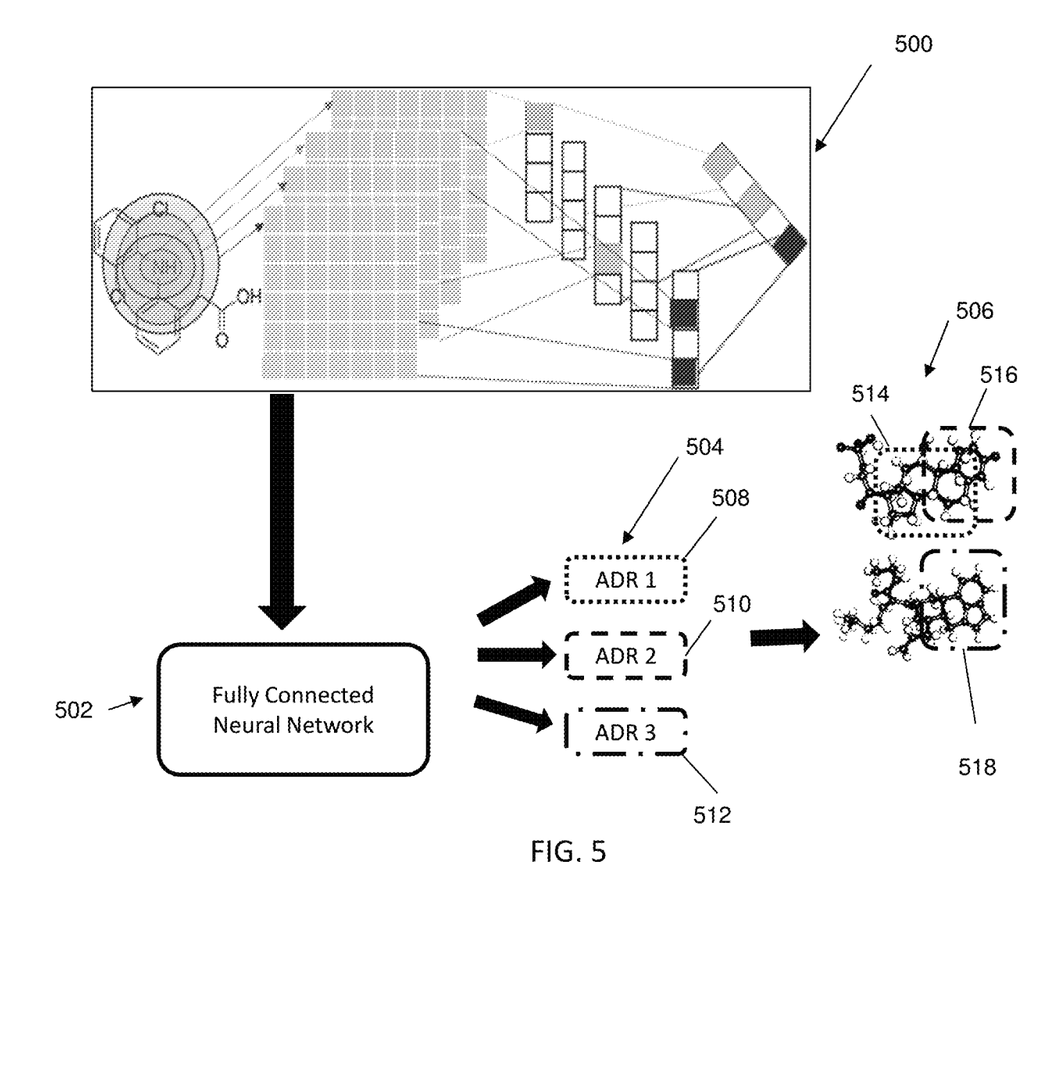
FIG. 5 illustrates an exemplary method according to one or more embodiments of the present invention.

FIG. 5 illustrates generation of substructure-ADR associations according to exemplary embodiments of the invention. For example, a combined learning framework using deep learning networks can be employed. As is shown at 500, molecular structures of drugs can be analyzed to generate fingerprint feature representations. Subsequently, as shown at 502, a fully connected neural network as a predictive model can be applied to the fingerprint feature representations. A plurality of ADRs 508, 510, 512 can be output, as is illustrated at 504, and associated at 506 with chemical substructures 514, 516, and 518, respectively.

Figure 6A:
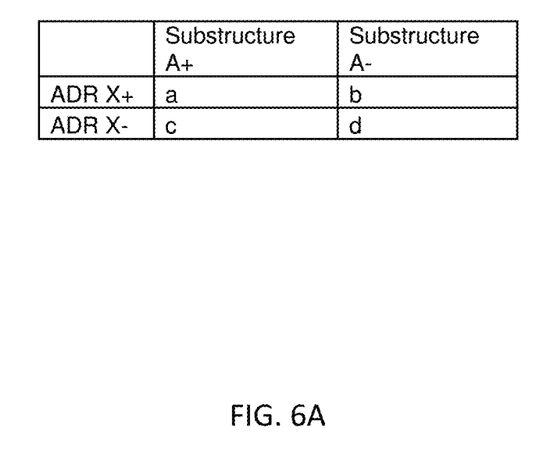
FIG. 6A illustrates an exemplary method according to one or more embodiments of the present invention.

Embodiments of the invention include determining significant substructure-adverse drug reaction associations. For example, FIG. 6A illustrates a confusion matrix calculated for a given substructure A regarding exemplary ADR X from a SIDER database. As is illustrated, a represents the number of drugs that contain substructure A and cause ADR X; b is the number of drugs that do not contain substructure A but trigger ADR X; c is the number of drugs that contain substructure A but have no association towards ADR X; and d is the number of drugs that do not contain substructure A and have no association towards ADR X. Some embodiments of the invention include calculating a p value using chi-squared tests and odds ratio to evaluate the association strength between substructure A and ADR X. In some embodiments of the invention, substructure-ADR associations are ranked based upon a statistical analysis.

Embodiments of the invention include grouping substructures and related ADRs using biclustering. For instance, substructures that are associated with the ADRs can be further grouped into higher levels because many of the ADRs are inherently related. For example, available ADRs can be classified into a hierarchical graph by organizing them from specific to generic categories.

For instance, to identify substructures that are responsible for a particular group of ADRs could provide an early guideline for avoiding those related substructures or their continuous spectrum of representations during drug development. Accordingly, significant substructure-ADR pairs can be grouped based upon a guilt by association principle. For example, significant substructure-ADR associations can be included in a bipartite graph, where substructures are represented in one layer and ADRs in another layer and, wherein an edge between them represents a significant association obtained from the previous step. Consequently, biclustering algorithms can be applied to find the higher level groupings (bi-cliques) of sub structure-ADR pairs.

Figure 6B:
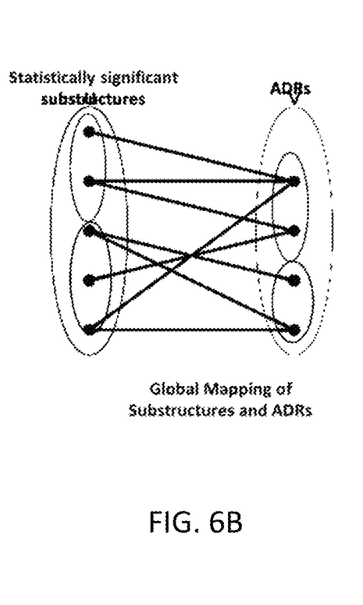
FIG. 6B illustrates an exemplary method according to one or more embodiments of the present invention.

FIG. 6B illustrates global mapping of substructures and ADRs. Statistically significant substructures can be mapped, for example graphically, to associated ADRs.

Figure 7:
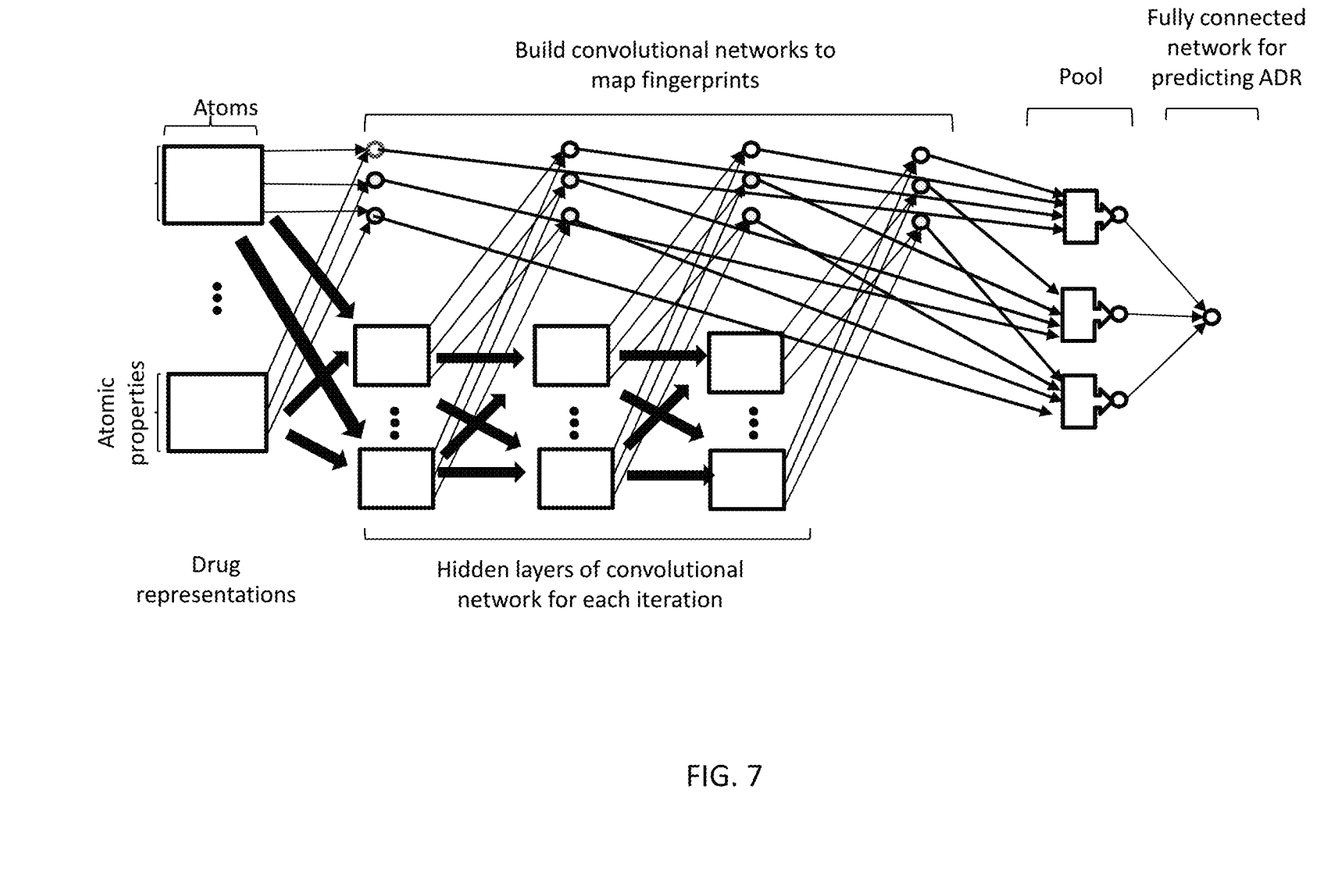
FIG. 7 illustrates an exemplary method according to one or more embodiments of the present invention.

FIG. 7 illustrates an exemplary combined learning framework using a deep learning network according to one or more embodiments of the invention. A plurality of drug representations including atoms and atomic properties can be obtained. These can be used to build convolutional networks to map fingerprints, as is illustrated. For example, building convolutional networks can be analogous or equivalent to hashing. Hidden layers of convolutional network can be included for each iteration (or radius). The exemplary framework can include pooling to generate final fingerprints. The final fingerprints can be used to generate a fully connected network for predicting an ADR.

Embodiments of the invention can automatically identify substructures of chemical compounds that have significant associations with ADRs using a deep learning approach, which can provide actionable insights for drug development and safety. Embodiments of the invention can rank substructure-ADR pairs obtained from deep learning models to systematically analyze the relationships among the groups of chemical substructures with groups of related ADRs using biclustering based machine learning techniques. Embodiments of the invention are useful for discovering relationships among chemical features and ADRs and can also be used for a small set of ADRs. Some embodiments of the invention can define chemical substructures without a-priori substructure definition. Embodiments of the invention can advantageously explore the statistical significance of chemical substructure-ADR pairs and their higher order groupings.

Embodiments of the invention can leverage a state-of the art convolutional deep learning network to simultaneously construct chemical fingerprints and their capabilities toward predicting ADR in a single learning framework. Such learning steps can result in a parsimonious set of fingerprints, for example, because the model can be limited to learn only those fingerprints that are predictive of ADRs, thus automatically filtering irrelevant fingerprints without post-processing.

Embodiments of the invention can be useful for predicting adverse drug reactions based upon chemical structure. Embodiments of the invention can also be used for other tasks in drug design, such as prediction of drug-drug interactions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:
1. A computer program analyzing adverse drug reactions, the computer program product comprising:
    a computer readable storage medium readable by a processing circuit and storing program instructions for execution by the processing circuit for performing a method comprising:
        receiving a plurality of drug chemical structures;
        receiving a plurality of known drug-adverse drug reaction associations;

constructing a deep learning framework for each of a plurality of adverse drug reactions based at least in part upon the plurality of drug chemical structures and the plurality of known drug-adverse drug reaction associations, wherein constructing the deep learning framework comprises defining a plurality of neighborhood-based fingerprints for each of the plurality of drug chemical structures using a plurality of hidden layers and generating a convolutional feature map comprising a plurality of convolutional steps, wherein each convolutional step encodes a respective neighborhood-based fingerprint at a respective hidden layer, wherein each fingerprint is obtained by starting from multiple atoms belonging to said fingerprint and resultant redundancies are removed by mapping each fingerprint into a lower dimension using a single layer of the deep learning framework;

analyzing the deep learning frameworks to determine a set of substructure-adverse drug reaction associations;

identifying a plurality of top predictive fingerprints for the set of sub structure-adverse drug reaction associations based upon learned weights from a final layer of the deep learning framework;

for each of the plurality of top predictive fingerprints, investigating each layer of the deep learning framework to identify atoms having a highest activation for the respective fingerprint;

reconstructing a set of substructures by starting from each identified atom and expanding the neighborhood up to the respective layer, wherein reconstructing from a first identified atom on a first layer of the deep learning framework results in expanding the respective neighborhood up to the first layer, and wherein reconstructing from a second identified atom on a second layer of the deep learning framework results in expanding the respective neighborhood up to the second layer;

calculating, for each substructure, a p value using a chi-squared test to evaluate a relative association strength between the substructure and the respective adverse drug reaction association;

ranking the substructure-adverse drug reaction associations according to statistical significance using the p values; and redesigning a candidate substructure of a candidate drug to avoid a determined substructure-adverse drug reaction association.

2. The computer program product according to claim 1, wherein the method further comprises grouping substructures and related adverse drug reactions with biclustering.

3. The computer program product according to claim 2, wherein the method further comprises outputting a chemical substructure-adverse drug reaction association.

4. The computer program product according to claim 2, wherein the method further comprises outputting a substructure-adverse drug reaction map.

5. A processing system for analyzing adverse drug reactions, comprising:

a processor in communication with one or more types of memory, the processor configured to:

receive a plurality of drug chemical structures;

receive a plurality of known drug-adverse drug reaction associations;

construct a deep learning framework for each of a plurality of adverse drug reactions based at least in part upon the plurality of drug chemical structures and the plurality of known drug-adverse drug reaction associations, wherein constructing the deep learning framework comprises defining a plurality of neighborhood-based fingerprints for each of the plurality of drug chemical structures using a plurality of hidden layers and generating a convolutional feature map comprising a plurality of convolutional steps, wherein each convolutional step encodes a respective neighborhood-based fingerprint at a respective hidden layer, wherein each fingerprint is obtained by starting from multiple atoms belonging to said fingerprint and resultant redundancies are removed by mapping each fingerprint into a lower dimension using a single layer of the deep learning framework;

analyze the deep learning frameworks to determine a set of substructure-adverse drug reaction associations;

identify one or more top predictive fingerprints for the set of substructure-adverse drug reaction associations based upon learned weights from a final layer of the deep learning framework;

for each of the one or more top predictive fingerprints, investigate each layer of the deep learning framework to identify atoms having a highest activation for the respective fingerprint;

reconstruct a set of substructures by starting from each identified atom and expanding the neighborhood up to the respective layer, wherein reconstructing from a first identified atom on a first layer of the deep learning framework results in expanding the respective neighborhood up to the first layer, and wherein reconstructing from a second identified atom on a second layer of the deep learning framework results in expanding the respective neighborhood up to the second layer;

calculate, for each substructure, a p value using a chi-squared test to evaluate a relative association strength between the substructure and the respective adverse drug reaction association;

rank the substructure-adverse drug reaction associations according to statistical significance using the p values; and redesigning a candidate substructure of a candidate drug to avoid a determined substructure-adverse drug reaction association.

6. The processing system according to claim 5, wherein the processor is configured to group substructures and related adverse drug reactions with biclustering.

7. The processing system according to claim 5, wherein the processor is configured to output a significant chemical substructure.

8. The processing system according to claim 5, wherein the processor is configured to output a substructure-adverse drug reaction map.

* * * * *